United States Patent [19]

Smith et al.

[11] Patent Number: 4,511,753

[45] Date of Patent: Apr. 16, 1985

[54] SELECTIVE REMOVAL OF VINYLIDENE OLEFIN FROM OLEFIN MIXTURES

[75] Inventors: R. Scott Smith, Baton Rouge; Gerald Z. Smith, Jr., Francisville, both of La.

[73] Assignee: Ethyl Corporation, Richmond, Va.

[21] Appl. No.: 570,934

[22] Filed: Jan. 16, 1984

[51] Int. Cl.$^3$ .............................................. C07C 7/17
[52] U.S. Cl. .................................. 585/856; 585/866; 568/72; 568/73
[58] Field of Search ............... 585/856, 864, 867, 866; 568/72, 73

[56] References Cited

U.S. PATENT DOCUMENTS

| | | | |
|---|---|---|---|
| 2,101,096 | 12/1937 | Reuter et al. | 568/73 |
| 2,386,770 | 10/1945 | Daley et al. | 568/73 |
| 2,386,771 | 10/1945 | Badertscher et al. | 568/73 |
| 2,386,772 | 10/1945 | Badertscher et al. | 585/856 |
| 2,426,648 | 9/1947 | Schulze et al. | 568/73 |
| 2,434,510 | 1/1948 | Olin et al. | |
| 2,443,852 | 6/1948 | Eaton et al. | |
| 2,468,739 | 5/1949 | Eaton et al. | |
| 2,481,583 | 9/1949 | Fenn et al. | 568/73 |
| 2,950,324 | 8/1960 | Loev et al. | 568/73 |
| 3,032,592 | 5/1962 | Frantz et al. | |
| 3,050,452 | 8/1962 | Louthan | |
| 3,083,231 | 3/1963 | Ray, Jr. | 568/73 |

OTHER PUBLICATIONS

Frantz, et al., "Chemical Engineering Progress", 59 No. 7, Jul. 1963.

Primary Examiner—Delbert E. Gantz
Assistant Examiner—Anthony McFarlane
Attorney, Agent, or Firm—Donald L. Johnson; John F. Sieberth; Joseph D. Odenweller

[57] ABSTRACT

Vinylidene olefins are selectively removed from a mixture of olefins containing vinylidene olefins by reacting the mixture with either hydrogen sulfide or a hydrocarbyl mercaptan and then distilling the resultant mixture to obtain a substantially vinylidene olefin-free product.

33 Claims, No Drawings

SELECTIVE REMOVAL OF VINYLIDENE OLEFIN FROM OLEFIN MIXTURES

BACKGROUND

Olefins, especially those in the 6–22 carbon number range, are useful chemical building blocks, for example, for making surfactant products. They can readily be converted to sulfonic acids by reaction with $SO_3$ or mixtures of $SO_2$ and oxygen. The alkali metal salts of the olefin sulfonic acids are very useful in detergents. U.S. Pat. No. 3,424,693 discloses the sulfonation of α-olefins followed by alkaline neutralization to form a useful surfactant. A similar process is disclosed in U.S. Pat. No. 3,860,528. Useful organic sulfonate surfactants can also be made by oxidizing an aliphatic hydrocarbyl mercaptan. Oxidation of alkyl mercaptan by reaction with oxygen in the presence of catalytic amounts of nitrogen oxide is disclosed in U.S. Pat. No. 2,505,910. Oxidation of sec-alkyl mercaptan with nitric acid to form sec-alkyl sulfonic acid which can be neutralized to form a surfactant is discussed in U.S. Pat. No. 2,187,335; U.S. Pat. No. 2,187,338 and U.S. Pat. No. 2,187,339.

The reaction of olefins with hydrogen sulfide to form mercaptan is known. U.S. Pat. No. 2,434,510; U.S. Pat. No. 2,443,852 and U.S. Pat. No. 2,468,739 disclose the reaction of olefins such as triisobutylene with hydrogen sulfide in the presence of an acid or metal halide catalyst to form sec/or tert-alkyl mercaptan. U.S. Pat. No. 3,050,452 discloses the reaction of olefins with hydrogen sulfide in the presence of a trialkyl phosphite using ultraviolet light as a catalyst.

Several commercial processes are available for producing olefins in the detergent range. Such olefins can be made by the thermal cracking of wax paraffins. They can also be made by catalyzed ethylene oligomerization or via chain growth on aluminum using Ziegler chemistry. The latter process involves the reaction of ethylene with triethylaluminum to form higher trialkylaluminum and the displacement of the alkyl groups from the aluminum to form olefin mixtures. These olefin mixtures are mainly linear α-olefins but contain lesser amounts of internal olefins and vinylidene olefins, the latter being 1,1-disubstituted ethylenes. In some cases it is desirable to remove the vinylidene olefins to obtain a mixture of linear α-olefins containing minor amounts of internal olefins to meet certain specific applications requirements. Since the vinylidene olefins boil in the same range as the linear α-olefins and internal olefins, they cannot be readily separated by distillation. Thus a need exists for a method of selectively separating vinylidene olefins from mixtures of olefins containing both vinylidene olefins and non-vinylidene olefins.

SUMMARY

It has now been discovered that mixtures of olefins containing both vinylidene olefins and non-vinylidene olefins such as linear α-olefins and internal olefins can be separated to obtain a substantially vinylidene olefin-free product by selectively reacting the vinylidene olefins with either hydrogen sulfide or an hydrocarbyl mercaptan in the presence of an acidic catalyst and then separating the linear α-olefins and internal olefins from the sulfided product, by various chemical or physical means, such as distillation.

DESCRIPTION OF THE PREFERRED EMBODIMENTS

The broadest embodiment of the invention is a process for selectively removing vinylidene olefins from a mixture containing vinylidene and non-vinylidene olefins wherein (a) said mixture of olefins is contacted with a sulfur compound selected from the group consisting of hydrogen sulfide and mercaptans (thiols) in the presence of an acidic catalyst to form a sulfided mixture, whereby said $H_2S$ selectively converts said vinylidene olefins to mercaptans and/or sulfides, and said mercaptan selectively converts said vinylidene olefins to a sulfide (thioether), and (b) separating the uncovered non-vinylidene olefins from said sulfided mixture by known physical and/or chemical methods.

A specific embodiment of the invention is a process for selectively removing vinylidene olefin from a mixture of olefins containing vinylidene olefins, a major portion of the vinylidene olefin having about the same boiling range as a major portion of the non-vinylidene olefins in said mixture, said process comprising (a) contacting said mixture of olefins with a sulfur compound selected from the group consisting of $H_2S$ and alkyl mercaptans in the presence of an acidic catalyst to form a sulfided mixture whereby said $H_2S$ selectively converts said vinylidene olefin to mercaptan and/or sulfide having a boiling point higher than said major portion of non-vinylidene olefins and said alkyl mercaptan selectively converts said vinylidene olefins to sulfide having a boiling range higher than said major portion of non-vinylidene olefins and (b) distilling said major portion of non-vinylidene olefins from said sulfided mixture.

In another embodiment of the invention the mercaptans formed along with sulfides by $H_2S$ addition to the olefin mixture are oxidized by known methods to dialkyl disulfides, thereby facilitating recovery of the unreacted substantially all linear olefins by distillation of the latter from the mixture. Suitable oxidizing agents are those that will oxidize the thiol groups to a straight chain aliphatic hydrocarbon group with little or no branching. Internal olefins can be represented by the structure

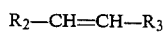

$$R_2-CH=CH-R_3$$

wherein $R_2$ and $R_3$ are straight or branched chain aliphatic hydrocarbon groups. Small amounts of internal olefins of the type

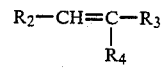

$$R_2-CH=C-R_3$$
$$\phantom{R_2-CH=C-}|$$
$$\phantom{R_2-CH=C-}R_4$$

wherein $R_2$ and $R_3$ are as defined above and $R_4$ is an alkyl group, may be present in the olefin mixtures. These are sometimes referred to as trialkylethylenes.

Examples of vinylidene olefins include 2-methyl-1-butene, 2-methyl-1-pentene, 2-ethyl-1-octene, 2-methyl-1-nonene, 2-butyl-1-decene, 2-propyl-1-octene, 2-ethyl-1-dodecene, 2-hexyl-1-decene, 2-ethyl-1-tetradecene, 2-ethyl-1-hexadecene, 2-methyl-1-heptadecene, 2-ethyl-1-octadecene, 2-butyl-1-hexadecene, 2-ethyl-1-eicosene, 2-butyl-1-octadecene, 2-ethyl-1-docosene, and the like.

Examples of the linear α-olefins are 1-hexene, 1-heptene, 1-octene, 1-nonene, 1-decene, 1-dodecene, 1-tridecene, 1-tetradecene, 1-hexadecene, 1-octadecene, 1-eicosene, 1-docosene, and the like. Of these the more preferred linear α-olefins are those containing about 6-22 carbon atoms.

Representative examples of internal olefins are the linear olefins 2-hexene, 3-heptene, 2-octene, 3-decene, 4-undecene, 4-dodecene, 2-tetradecene, 3-tetradecene, 2-hexadecene, 7-hexadecene, 2-octadecene, 3-eicosene, 8-docosene, 2-tricosene, 3-tetracosene, and the like. Examples of the trialkylethylene type of internal olefin include 3-methyl-2-heptene, 3-methyl-3-heptene, 3-methyl-3-nonene, 5-methyl-4-undecene, and the like.

In the preferred embodiments of this invention, the olefin mixtures are of the type formed by ethylene oligomerization or ethylene chain growth on aluminum. Thus they will contain all form disulfides but not oxidize any substantial amount of the olefins. Examples include oxygen, cupric chloride, lead sulfide plus air, sodium hypochlorite and doctor solution (alkaline sodium plumbite plus small amount of sulfur).

Another embodiment of the invention involves removal of the mercaptans formed along with sulfides by H₂S addition to the olefin mixture by extraction with a suitable solvent, such as an alkanolamine such as triethanolamine, leaving a mixture of sulfide and substantially all linear olefin, from which the latter can readily be separated by distillation.

When the sulfided products are all dialkyl sulfides or a mixture of dialkyl sulfides and dialkyl disulfides, application of the process to mixtures of at least two successive even carbon number olefins is facilitated, since said sulfide and disulfide components will have substantially lower vapor pressures than both of the olefins, which can be readily separated by distillation.

Any mixture of olefins containing vinylidene olefins in addition to non-vinylidene olefins can be effectively separated by the present process. Such olefin mixtures can contain α-olefins, especially linear α-olefins, internal olefins and vinylidene olefins. Vinylidene olefins have the structure

wherein R represents the same or different aliphatic hydrocarbon group. Alpha-olefins have an olefinic double bond at the end of the hydrocarbon chain. They are sometimes called vinyl olefins. They can be represented by the structure

wherein $R_1$ represents a straight or branched chain aliphatic hydrocarbon group. In a more preferred embodiment $R_1$ is mainly even carbon numbered species; R, $R_1$, $R_2$ and $R_3$ in the vinylidene olefins, linear α-olefins and linear internal olefins in the mixtures will be even carbon numbered alkyl groups; and the small amounts of trialkylethylene components will have resulted from isomerization of the even carbon numbered vinylidenes.

In a still more preferred embodiment, the mixture of olefins comprises a major portion of linear α-olefins containing about 6-22 carbon atoms and a minor amount of vinylidene olefins. The mixture may also contain minor amounts of internal olefins. In a most preferred embodiment the olefin mixture comprises a major amount of linear α-olefins containing about 10-18 carbon atoms and a minor amount up to about 35 weight percent of vinylidene olefins and optionally contains minor amounts of internal olefins.

The process is carried out by contacting the olefin mixture with either hydrogen sulfide or a mercaptan in the presence of an acidic catalyst which term includes the various Lewis and Bronsted acids.

When hydrogen sulfide is used as the sulfiding agent, the vinylidene olefin in the mixture of olefins must be such that when selectively reacted with hydrogen sulfide to form a mercaptan, a major amount of the resultant mercaptan will have a boiling point higher than the boiling point of at least a major amount of the non-vinylidene olefins in the mixture of olefins. Preferably at least 80 weight percent of the resultant mercaptan will have a boiling point higher than at least 80 weight percent of the non-vinylidene olefins. More preferably, substantially all of the resultant mercaptans will have a boiling point higher than at least 80 weight percent of the non-vinylidene olefins. Still more preferably, substantially all of the resultant mercaptans will have a boiling point higher than at least 90 weight percent of the non-vinylidene olefins. In a most preferred embodiment, substantially all of the resultant mercaptan will have a boiling point higher than substantially all of the non-vinylidene olefins such that substantially all of the non-vinylidene olefins can be distilled from the sulfided mixture without distillation of any substantial amount of the resultant mercaptan.

When using hydrogen sulfide as the sulfiding agent, the proper boiling point relationship can be obtained if a major amount of the vinylidene and non-vinylidene olefins contain the same number (designated n) of carbon atoms wherein n can be any integer from about 6-22, more preferably 10-18. More preferably, at least 80 weight percent of the vinylidene and non-vinylidene olefins should contain the same number of carbon atoms and still more preferably at least 90 weight percent of the vinylidene and non-vinylidene olefins should contain the same number of carbon atoms. In a most preferred embodiment, when using hydrogen sulfide the olefin mixture is a single distillation cut wherein substantially all of the vinylidene and non-vinylidene olefins contain about the same number of carbon atoms.

As indicated above, the mercaptans present in the sulfided products formed by hydrogen sulfide addition along with sulfides can be removed from the olefin and sulfided product mixture by physical methods such as extraction, adsorption, and the like, or can be oxidatively converted to dialkyl disulfides. Mild chemical oxidants such as doctor solution are effective in the mercaptan-to-disulfide conversion, and air oxidation can be employed under certain conditions. The unreacted essentially all linear olefins in the product mixtures are more readily removable by distillation from the disulfides than from the higher vapor pressure mercaptans.

When hydrogen sulfide is used as the sulfiding agent, the amount of hydrogen sulfide should be an amount which is sufficient to convert the vinylidene olefin content of the olefin mixture to a sulfide or mercaptan. Theoretically, one-half mole of hydrogen sulfide can convert one mole of vinylidene olefin to a sulfide. In practice, it is preferred to carry out the process so as to consume from about 0.5 to about 1.1 moles of hydrogen sulfide per mole of vinylidene olefin in the olefin mixture. A most preferred range is about 0.5 to 0.6 mole of hydrogen sulfide consumed per mole of vinylidene olefin.

When using a mercaptan as the sulfiding agent, the carbon number range in the olefin mixture can be much broader because the mercaptan can be selected such that when it selectively reacts with the vinylidene olefins, it will form a sulfide that will boil above at least a major amount of the non-vinylidene olefins such that the major amount of non-vinylidene olefins can be effectively distilled from the sulfided vinylidene olefins. Preferably, the mercaptan sulfiding agent is selected such that the sulfides formed in the sulfided mixture will have a boiling range higher that at least 80 weight percent, more preferably 90 weight percent and most preferably substantially all of the nonvinylidene olefins in the olefin mixture.

Useful mercaptans include any mercaptan which will selectively react with vinylidene olefins to form a sulfide. Examples of mercaptans include methyl mercaptan, n-butyl mercaptan, sec-butyl mercaptan, isobutyl mercaptan, tert-butyl mercaptan, thiophenol, benzyl mercaptan, α-methylbenzyl mercaptan, α,α-dimethylbenzyl mercaptan, and the like. The preferred mercaptans are the alkyl mercaptans such as methyl mercaptan, isobutyl mercaptan, n-butyl mercaptan, 2-ethylheptyl mercaptan, sec-butyl mercaptan, tert-butyl mercaptan, 2-ethylhexyl mercaptan, n-dodecyl mercaptan, 2-mercaptododecane, n-octadecyl mercaptan, 3-mercaptooctadecane, 2-ethylhexadecyl mercaptan, 2-ethyl-2-mercaptohexadecane, eicosyl mercaptan, docosyl mercaptan, tetracosyl mercaptan and the like. In certain cases it is desirable to use a mixture of secondary and tertiary alkyl mercaptans prepared by acid-catalyzed addition of hydrogen sulfide to olefin mixtures of the type from which vinylidene olefins are being removed by the process of this invention.

Aliphatic dimercaptan compounds can also be used. In this case the quantity of mercaptan will be a function of the number of mercaptan groups. In other words, one mole of a dimercaptan will represent two equivalents of mercaptan and only require about one half as much mercaptan on a molar basis as a mole of a monomercaptan. Examples of such dimercaptans are 1,2-dimercapto ethane, 1,2-dimercapto propane, 1,3-dimercapto propane, 1,6-dimercapto hexane, and the like.

The most preferred mercaptans are the alkyl mercaptans which contain from 1 to about 22 carbon atoms. In a still more preferred embodiment, the alkyl mercaptan contains about 10-20 carbon atoms.

Acidic catalysts that can be used include such acids as sulfuric acid, phosphoric acid, HF, HCl, HBr, aromatic sulfonic acids such as para-toluenesulfonic acid, benzenesulfonic acid, napthalenesulfonic acid, aliphatic sulfonic acids such as methanesulfonic acid, ethanesulfonic acid, hexanesulfonic acid, dodecanesulfonic acid, octadecanesulfonic acid and the like. Ammonium salts of strong acids can also be used such as ammonium chloride, ammonium bromide, ammonium sulfate and the like.

Lewis acid metal halide catalysts are also very effective. Representative examples of these include boron trichloride, boron trifluoride, stannic chloride, zinc chloride, ferric chloride, aluminum chloride, aluminum bromide, and the like.

The amount of catalyst need only be a small amount. A useful range based upon the weight of the olefin mixture is about 0.01 to 5.0 weight percent. A more preferred concentration of catalyst is about 0.2 to 1 weight percent.

The sulfiding reaction is preferably carried out by injecting the hydrogen sulfide plus catalyst into the olefin mixture or adding the mercaptan plus catalyst to the olefin mixture while stirring at reaction temperatures. The temperature should be high enough to cause the hydrogen sulfide or mercaptan to react with the vinylidene olefin but should not exceed the boiling point of the reactants. A useful temperature range is from about $-10°$ C. toabout $60°$ C. A more preferred temperature range is about $-10°$ to $20°$ C. Most preferably the reaction is conducted at a temperature slightly above the freezing point of the olefin mixture. External heat application is not necessary but may be used to control temperature. Generally, a small amount of cooling will be required to control the temperature at the desired range.

It is advantageous in the process of this invention to minimize time of contact between olefin and acid catalyst in the absence of $H_2S$ or mercaptan sulfiding agent, in order to prevent or limit the extent of unwanted side reactions such as olefin oligomerization or isomerization. Thus the preferred procedures for introducing catalyst are addition of catalyst to a mixture of olefin and sulfiding agent, addition of a mixture of catalyst and sulfiding agent to the olefin, addition of olefin to a mixture of catalyst and sulfiding agent, or, if catalyst is first added to the olefin, immediately adding the sulfiding agent with a minimum time lapse.

After the olefin mixture has been reacted with hydrogen sulfide and/or mercaptan, the catalyst is deactivated with a small amount of an alkaline material such as sodium hydroxide, potassium hydroxide, sodium carbonate, ammonium hydroxide, and the like. The neutralized mixture can be water washed if desired but this is not necessary. The mixture can then be distilled to separate the non-vinylidene olefins. The vinylidene olefins have been selectively reacted with either hydrogen sulfide or mercaptan to form higher molecular weight compounds (e.g. mercaptans or sulfides) which will boil at a higher temperature than the non-vinylidene olefins. The distillation may be carried out at atmospheric pressure or under reduced pressure depending upon the boiling point of the olefin mixture. With mixtures of low molecular weight olefins, such as pentene, hexene and heptene, the distillation can be carried out at atmospheric pressure or at only moderately reduced pressure. With olefin mixtures of higher molecular weight such as mixtures of hexadecene and octadecene, the distillation is preferably carried out under vacuum, for example, at absolute pressures of about 1-10 mm Hg.

The distillation is carried on until most of the non-vinylidene olefins have been removed. The residue will contain the vinylidene olefins which have now been converted to mercaptans and/or sulfides. Essentially quantitative removal of vinylidene olefins from mixtures of linear α-olefins and internal olefins can be achieved by the present process.

The present process, when $H_2S$ is employed, and the olefins are recovered by distillation from the mercaptan and sulfide products formed, is most useful in removing vinylidene olefins from a mixture of olefins which are all substantially the same molecular weight. For example, the process is very effective in removing $C_{14}$ vinylidene olefins from a mixture of $C_{14}$ olefins containing vinylidene olefins, α-olefins and internal olefins. If the mixture contains higher olefins in addition to the $C_{14}$ olefins, for example $C_{16}$ olefins, the mercaptan formed by reacting hydrogen sulfide with the $C_{14}$ vinylidene olefin can boil very close to the non-sulfided $C_{16}$ non-vinylidene olefins. Therefore, in a preferred embodiment when using hydrogen sulfide as the sulfiding agent the olefins in the mixture are mainly of about the same molecular weight. In other words, the olefin mixture should consist mainly of, for example, $C_{14}$ olefins and only minor amounts of $C_{16}$ olefins. Likewise, if the main component is $C_{16}$ olefin, the mixture should contain only minor amounts up to about 10 weight percent of $C_{18}$ olefins. However, as indicated above, when a mixture of carbon numbers is used, the mercaptan can be removed from the sulfided mixture by physical methods such as extraction, adsorption, and the like, or can be converted in the mixture to a higher boiling derivative such as a dialkyl disulfide, from which a broader carbon number range of unreacted essentially all linear olefins can be separated by distillation.

In the process when a mercaptan is used as the sulfiding agent the reaction of olefin with mercaptan forms a sulfide which can have a much higher molecular weight and thus a much higher boiling point than unreacted olefins. For example, in a blend of $C_{14}$ and $C_{16}$ olefins containing both vinylidene olefins and linear $\alpha$-olefins, the sulfide formed by reacting the mixture with, for example, a mixture of secondary tetradecyl mercaptans will convert the $C_{14}$ vinylidene olefin to sulfides having a substantially higher boiling point than the $C_{16}$ linear $\alpha$-olefin. Thus, even the $C_{16}$ $\alpha$-olefins can be distilled from the sulfided mixture without being contaminated with the sulfided $C_{14}$ vinylidene olefin.

The following examples serve to show how the process is carried out.

EXAMPLE 1

In a reaction vessel was placed 246 grams of an olefin mixture containing 74 weight percent linear $\alpha$-hexadecene, 6 weight percent internal hexadecene and 20 weight percent $C_{16}$ vinylidene olefin. To this mixture was added 24 grams concentrated $H_2SO_4$ and the mixture was stirred while injecting gaseous $H_2S$ at ambient temperature. Rapid $H_2S$ uptake took place during the first 20 minutes and the temperature rose from ambient temperature to 45° C. The reaction mixture was then cooled with an ice bath to 20° C., causing the $H_2S$ uptake to subside. The mixture was warmed back up to 45°-50° C. but $H_2S$ uptake continued only at a much slower rate. NMR analysis of the organic phase showed that the vinylidene olefin content had been completely converted to a non-olefinic compound.

EXAMPLE 2

In a reaction vessel was placed 300 mL of $C_{16}$ olefin which consisted mainly of 71.5 weight percent linear $\alpha$-olefins, 7.5 weight percent internal olefins, and 21 weight percent vinylidene olefins. To this was added 5 mL sulfuric acid following which hydrogen sulfide was bubbled through the stirred reaction mixture at about 5° C. for 5 minutes. The resultant sulfided reaction mixture was washed with water and distilled to remove 145.6 grams (0.65 moles) of non-vinylidene olefin (88 weight percent $\alpha$-olefin and 12 weight percent internal olefin by NMR). The distillation was continued to recover a mixture of mercaptan and sulfide formed by reacting the $H_2S$ with the vinylidene olefins. This gave 0.17 moles of mercaptan and 0.06 moles of sulfide.

EXAMPLE 3

In a reaction vessel was placed 1055 grams of a mixture of hexadecenes containing 21 weight percent vinylidene olefins, 7.5 weight percent internal olefins, and 71.5 weight percent $\alpha$-olefins. The reaction vessel was equipped with a condenser, gas bubbler, dropping funnel and gas eduction tube. The stirred reaction mixture was maintained at 10°-15° C. using an ice bath and $H_2S$ was bubbled through the mixture while adding 52.8 grams of sulfuric acid from the dropping funnel over a 5 minute period. The reaction of the $H_2S$ was rapid as evidenced by lack of any escaping $H_2S$ gas. $H_2S$ addition was continued until $H_2S$ gas began to evolve indicating that reaction with the vinylidene olefins was complete. Residual $H_2S$ was removed from the system using a nitrogen purge. The reactor contents were transferred to a separatory funnel and the sulfuric acid layer was drained. The olefin layer was washed twice with 200 mL portions of a 50% aqueous ethanol solution. The sulfided olefin mixture was dried over a mixture of sodium carbonate and magnesium sulfate and filtered. A vinylidene-free olefin product was recovered by flash distillation at 1 mm Hg pressure.

The procedure of this example was repeated using a mixture of tetradecenes. A vinylidene-free olefin product was recovered by flash distillation under vacuum.

EXAMPLE 4

Into a reaction vessel was placed 632 grams of a mixture of tetradecenes and hexadecenes containing vinylidene olefins, internal olefins and $\alpha$-olefins. To this was added 130.1 grams of a mixture of 37 weight percent hexadecyl mercaptan and 63 weight percent octadecyl mercaptan. This amount of mercaptan was calculated to be the mole equivalent of the moles of vinylidene olefins in the olefin mixture. At this time, 3.7 grams of sulfuric acid was added and the mixture was stirred at room temperature for four hours. The reaction was observed to be mildly exothermic. After the sulfiding reaction, the acid catalyst was neutralized with aqueous sodium hydroxide and the $C_{14}$ and $C_{16}$ olefins were recovered from the sulfided mixture by flash distillation under vacuum at 0.5 mm Hg pressure. The starting olefin mixture contained 80.4 weight percent $\alpha$-olefins (vinyl olefins), 4.4 weight percent internal olefins and 15.2 weight percent vinylidene olefins. The flash distillate was found to contain 91.2 weight percent $\alpha$-olefins (vinyl olefins), 5.7 weight percent internal olefins and only 3.1 weight percent vinylidene olefins.

EXAMPLE 5

Into a reaction vessel was placed 364 grams of a mixture of hexadecenes containing 71.5 weight percent 1-hexadecene, 21 weight percent vinylidene isomers, and 7.5 weight percent linear internal isomers. The reaction vessel was equipped with a stirring motor, gas dispersion tube, and a gas bubbler at the reactor outlet. The stirred hexadecenes were cooled to $-5°$ C. with an ice bath. $H_2S$, 11.6 grams, was charged to a gas cylinder, which was then connected to the gas dispersion tube. Aluminum chloride, 4 grams, was added to the hexadecenes. Rapid addition of $H_2S$ was begun immediately. $H_2S$ reaction began within seconds, and the addition was complete in one minute, after which the catalyst was killed by the addition of water. NMR analysis of the product mixture showed the unreacted olefin to be 87.6 mole percent linear 1-hexadecene and 12.5 mole percent linear internal hexadecenes. No branched olefins were detected. Olefin conversion was approximately 23 mole percent, as determined by both NMR and GLC.

EXAMPLE 6

A mixture of hexadecenes, 394 g, containing 21 weight percent vinylidene isomers, was charged to a 1-L autoclave. $H_2S$, 6.3 g, was fed from a small cylinder, through a second small cylinder containing 2 g $BF_3$, into the autoclave. The mixture was stirred for 20 minutes while cooling with tap water, after which the reactor was vented and 20 mL water was added to deactivate the catalyst. The organic phase was washed with 200 mL $H_2O$. NMR analysis of the product showed that 14% of the olefin had been converted to mercaptan or thioether. The remaining unreacted olefin had a composition of 78% vinyl olefin, 12% internal olefin, and 10% trisubstituted ethylenes. Thus the vinylidene olefin content had been decreased by formation of sulfided products and partial isomerization to trialkylethylene isomers.

EXAMPLE 7

To 100 g of a mixture consisting of 82.6% $C_{16}$ olefins, 8.4% $C_{16}H_{33}SH$, and 9% $(C_{16}H_{33})_2S$ in a 250 mL Erlenmeyer flask was added 10 g of 50% aqueous caustic. A magnetic stirring bar was added and the mixture was stirred and heated at 90°–110° C. for 4 hours while bubbling in air. After cooling the mixture, GLC analysis showed that the mercaptan had been quantitatively converted to dihexadecyl disulfides.

As the above examples show, the present process provides an effective way to lower or eliminate the vinylidene olefins from a mixture of olefins containing vinylidene olefins.

We claim:

1. A process for selectively removing vinylidene olefins containing about 6–22 carbon atoms from a mixture of olefins containing vinylidene olefins and non-vinylidene olefins, said process comprising
   (a) contacting said mixture of olefins in the liquid phase with a sulfur compound selected from the group consisting of $H_2S$ and mercaptans in the presence of an acidic catalyst to form a sulfided mixture whereby said $H_2S$ selectively converts said vinylidene olefins to mercaptans, sulfides, or mixtures thereof, said mercaptan selectively converts said vinylidene olefins to a sulfide (thioether) and
   (b) separating said non-vinylidene olefins from said sulfided mixture.

2. A process of claim 1 for selectively removing vinylidene olefins from a mixture of olefins containing vinylidene olefins and a major portion of that vinylidene olefin having about the same boiling range as a major portion of the non-vinylidene olefins in said mixture, said process comprising
   (a) contacting said mixture of olefins with a sulfur compound selected from the group consisting of $H_2S$ and mercaptans in the presence of an acidic catalyst to form a sulfided mixture whereby said $H_2S$ selectively converts said vinylidene olefins to mercaptans, sulfides, or mixtures thereof, having a boiling point higher than said major portion of non-vinylidene olefins, and said mercaptan selectively converts said vinylidene olefins to a sulfide having a boiling range higher than said major portion of non-vinylidene olefins and
   (b) distilling said major portion of non-vinylidene olefins from said sulfided mixture.

3. A process of claim 1 wherein said sulfur compound is $H_2S$.

4. A process of claim 3 wherein said mixture of olefins contains a major amount of linear $\alpha$-olefins and a minor amount up to about 35 weight percent of vinylidene olefin.

5. A process of claim 1 wherein said sulfur compound is an alkyl mercaptan containing about 1–22 carbon atoms.

6. A process of claim 5 wherein said mixture of olefins contains a major amount of linear $\alpha$-olefins and a minor amount up to about 35 weight percent of vinylidene olefins.

7. A process of claim 1 wherein said acidic catalyst is selected from the group consisting of sulfuric acid, aromatic sulfonic acids, aliphatic sulfonic acids, phosphoric acid and Lewis acid metal halides.

8. A process of claim 7 wherein said catalyst is sulfuric acid.

9. A process of claim 8 wherein said sulfur compound is $H_2S$.

10. A process of claim 9 wherein said mixture of olefins contains a major amount of linear $\alpha$-olefins and a minor amount up to about 35 weight percent of vinylidene olefins.

11. A process of claim 7 wherein said catalyst is $BF_3$.

12. A process of claim 11 wherein said sulfur compound is $H_2S$.

13. A process of claim 7 wherein said catalyst is $AlCl_3$.

14. A process of claim 13 wherein said sulfur compound is $H_2S$.

15. A process of claim 3 wherein at least 80 weight percent of said vinylidene olefins and said non-vinylidene olefins contain 6 to about 22 carbon atoms and a major portion of said non-vinylidene olefins are linear $\alpha$-olefins.

16. A process of claim 15 wherein said vinylidene olefins and said non-vinylidene olefins contain 10 to about 18 carbon atoms.

17. A process of claim 5 wherein said alkyl mercaptan is selected to contain sufficient carbon atoms such that the sulfides in said sulfided mixture formed by reaction of said alkyl mercaptan with said major portion of vinylidene olefins have a boiling range that is higher than the boiling range of at least 80 weight percent of said non-vinylidene olefins.

18. A process of claim 17 wherein said mixture of olefins contains a major amount of linear $\alpha$-olefins and a minor amount up to about 35 weight percent of vinylidene olefins.

19. A process of claim 18 wherein said acidic catalyst is sulfuric acid.

20. A process of claim 18 wherein said acidic catalyst is $BF_3$.

21. A process of claim 18 wherein said acidic catalyst is $AlCl_3$.

22. A process of claim 18 wherein said mixture of olefins consists of at least 90 weight percent of dodecenes and tetradecenes.

23. A process of claim 18 wherein said mixture of olefins consists of at least 90 weight percent of tetradecene and hexadecenes.

24. A process of claim 18 wherein said mixture of olefins consist of at least 90 weight percent of hexadecenes and octadecenes.

25. A process of claim 18 wherein said mixture of olefins consist of at least 90 weight percent of tetradecenes, hexadecenes, and octadecenes.

26. A process of claim 3 wherein said mercaptans formed by reaction of $H_2S$ with said vinylidene olefins are reacted with an oxidizing agent to form disulfides and said separating is conducted by distilling said non-vinylidene olefins from said disulfides.

27. A process of claim 26 wherein said oxidizing agent is lead sulfide plus air.

28. A process of claim 26 wherein said oxidizing agent is doctor solution.

29. A process of claim 26 wherein said oxidizing agent is cupric chloride.

30. A process of claim 1 wherein said sulfur compound is $H_2S$ and said mercaptans formed by reaction of said vinylidene olefins with said $H_2S$ are separated by extraction with an alkanolamine solvent.

31. A process of claim 30 wherein said alkanolamine is triethanolamine.

32. A process of claim 31 wherein after extraction of said mercaptans, said non-vinylidene olefins are distilled from the resultant extracted sulfided mixture.

33. A process of claim 1 conducted at a temperature in the range of about $-10°$ to $20°$ C.

* * * * *

UNITED STATES PATENT AND TRADEMARK OFFICE
CERTIFICATE OF CORRECTION

PATENT NO. : 4,511,753
DATED : APRIL 16, 1985
INVENTOR(S) : R. SCOTT SMITH, ET AL.

It is certified that error appears in the above-identified patent and that said Letters Patent is hereby corrected as shown below:

Column 2, line 14, reads "uncovered" and should read -- unconverted --.

Column 2, lines 41 through Column 3, line 15 from "a straight" to "contain all" should be moved to appear in Column 3, line 54 after "is mainly".

Column 3, line 44, reads "wherein R" and should read -- wherein each R --.

Column 6, line 11, reads "toabout" and should read -- to about --

Column 6, line 53, reads "mm Hg" (in bold letters) and should read -- mm Hg -- (in regular letters).

Signed and Sealed this

Tenth Day of September 1985

[SEAL]

Attest:

DONALD J. QUIGG

Attesting Officer    Acting Commissioner of Patents and Trademarks - Designate